United States Patent [19]

Corn

[11] 4,080,374
[45] Mar. 21, 1978

[54] PRODUCT RECOVERY
[75] Inventor: John William Corn, Orange, Tex.
[73] Assignee: E. I. Du Pont de Nemours and Company, Wilmington, Del.
[21] Appl. No.: 771,065
[22] Filed: Feb. 23, 1977
[51] Int. Cl.² .......................................... C07C 120/02
[52] U.S. Cl. ........................... 260/465.3; 260/465.8 R; 260/465.9
[58] Field of Search ..................... 260/465.3, 465.8 R, 260/465.9

[56] References Cited

U.S. PATENT DOCUMENTS

| | | | |
|---|---|---|---|
| 3,496,215 | 2/1970 | Drinkard, Jr. et al. | 260/465.3 X |
| 3,526,654 | 9/1970 | Hildebrand | 260/465.8 X |
| 3,538,142 | 11/1970 | Drinkard, Jr. et al. | 260/465.9 |
| 3,542,847 | 11/1970 | Drinkard, Jr. et al. | 260/465.3 X |
| 3,676,475 | 7/1972 | Drinkard, Jr. | 260/465.8 X |
| 3,697,578 | 10/1972 | Pasquino et al. | 260/465.9 |
| 3,752,839 | 8/1973 | Drinkard, Jr. et al. | 260/465.3 X |

Primary Examiner—Joseph Paul Brust

[57] ABSTRACT

Process for the recovery of reactants and products from a catalyst containing residue, e.g., a residue obtained from the hydrocyanation of olefins such as butadiene using a zero-valent nickel complex as the hydrocyanation catalyst wherein the complex is promoted with a triarylborane or a zinc compound such as zinc chloride. The residue is mixed, i.e., extracted with a solvent consisting essentially of monoolefinically unsaturated nitriles, e.g., 3-pentenenitrile. The resulting extract containing the pentenenitriles and the desired products, e.g., adiponitrile and its precursors is separated from the insoluble materials consisting essentially of catalyst residue and at least a portion thereof is returned to the hydrocyanation process.

4 Claims, 1 Drawing Figure

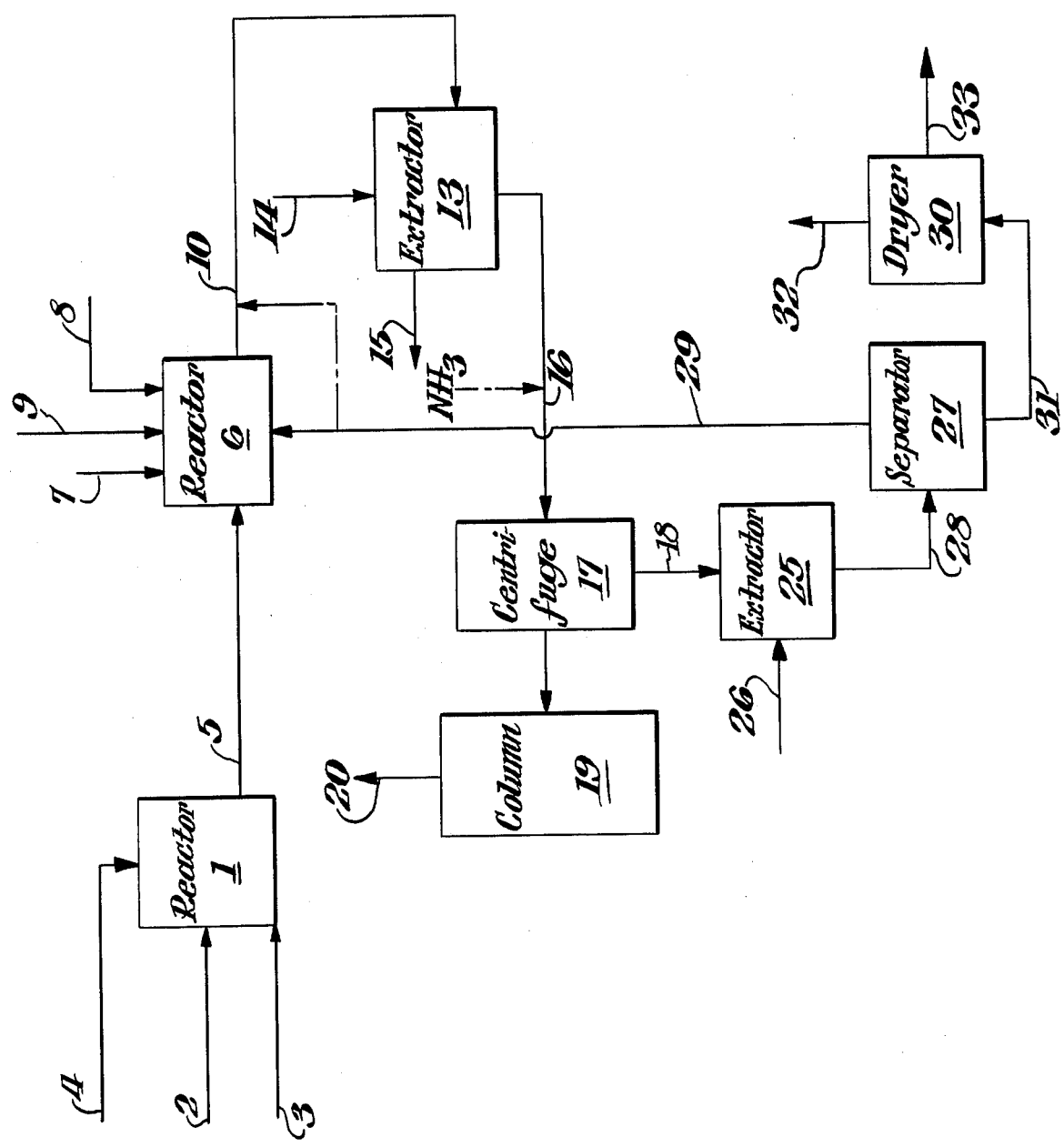

PRODUCT RECOVERY

BACKGROUND OF THE INVENTION

1. Field of the Invention

The present invention relates to an extraction process for recovering intermediates and product from a process residue and more particularly, to a process for the recovery of adiponitrile and its precursors from a process residue obtained from the preparation of adiponitrile by the hydrocyanation of butadiene.

2. Description of the Prior Art

A general disclosure of typical processes to which the present invention may be applied is found in the publication entitled "Hexamethylene Diamine" in The Process Economics Program Report No. 31-A, Stanford Research Institute, Menlo Park, C.A.; September, 1972. More particularly, the hydrocyanation process to which the present invention can be applied is disclosed in U.S. Pat. Nos. 3,496,215 issued on Feb. 10, 1970 3,496,218 issued on Feb. 17, 1970 3,542,847 issued on Nov. 24, 1970 and 3,752,839 issued on Aug. 14, 1973. The residue from the above-disclosed process is obtained by removing the substantial portion of desired products, unreacted materials and intermediates from the reactor effluent, separating solvent and other volatiles from the resultant stream for recycle to the reactor and thereafter obtaining a concentrated waste system as residue. The process of the present invention recovers valuable products from such residue.

Solvent extraction for recovery of organics has been considered extensively, e.g., Separation Processes, King, C.J., Chem. Eng. Series, McGraw Hill, 1971, but has not been applied to the type of waste stream herein disclosed using the claimed solvents. Common solvents are foreign to the hydrocyanation system and must be rigorously separated from the extract before the extract can be returned to the system. Such a procedure is unsatisfactory in the commercial operation to which the present invention is applied.

SUMMARY OF THE INVENTION

An extraction process for the recovery of organic nitriles especially organic dinitriles e.g., adiponitrile from a waste stream containing products, by-products and catalyst residue obtained from a process for the production of adiponitrile by the catalytic hydrocyanation of butadiene in the presence of a zero-valent nickel catalyst which process comprises extracting e.g., by mixing one part of said waste stream which at least 0.5 parts of an extractant consisting essentially of organonitriles boiling below about 250° C at atmospheric pressure and especially organonitriles having an average of about 5-10 carbon atoms, e.g., olefinically unsaturated nitriles selected from the class consisting of 3-pentenenitrile, 2-pentenenitrile and mixtures thereof, separating the resultant extract from the insoluble material and thereafter returning at least a portion of the extract to the hydrocyanation process.

BRIEF DESCRIPTION OF THE DRAWING

The drawing attached hereto and made a part of this specification is a schematic of a hydrocyanation process which produces a waste stream containing catalyst residue and the process of the present invention which treats that stream.

DETAILED DESCRIPTION OF THE INVENTION

The process of the present invention is applied to a waste stream from a process which involves the direct addition of two molecules of hydrogen cyanide to a molecule of butadiene thereby producing adiponitrile. The process is conducted in two steps. With reference to the drawing, the first step (reactor 1) involves the addition of one molecule of hydrogen cyanide (stream 2) to dry butadiene (stream 3) in the presence of a catalyst (stream 4) consisting of zero-valent nickel usually in the form of a nickel tetrakis-tritolylphosphite, to produce a mixture of cis- and trans-3-pentenenitrile and 4-pentenenitrile. This reaction mixture is withdrawn from reactor 1 via line 5, treated to remove impurities and then introduced into reactor 6 along with additional HCN (line 7), ligand (line 8) and catalyst promoter such as zinc chloride or preferably, a triarylborane such as triphenylborane. In this reaction which can be conducted in one or more steps, 4-pentenenitrile is formed by the in situ isomerization of 3-pentenenitrile. The 4-pentenenitrile is then converted to adiponitrile by the addition of one molecule of HCN. The effluent from the reactor 6 is passed to extractor 13 and there contacted with cyclohexane (line 14). The cyclohexane extractant (line 15) is subsequently directed to further treatment for product recovery. During the hydrocyanation as described as hereinabove a portion of the zero-valent nickel catalyst is oxidized to nickel cyanide which is insoluble in the reaction medium and which forms insoluble complexes with the triarylborane or zinc promoter. The tails from the extraction vessel (line 16) contain such complexes which are subsequently separated from the tails (line 16) by centrifuge 17, the discharge of which (line 18) is the sludge or slurry to which the present invention is applied. Ammonia can be introduced into line 16 as indicated to enhance precipitation of zinc when a zinc promoter is employed. A typical analysis of this sludge is set forth below in Table I.

TABLE I

SLURRY COMPOSITION
(% by weight)

| ZnCl$_2$ | | PROMOTER Triphenylborane | |
| --- | --- | --- | --- |
| Zn(NH$_3$)$_2$Cl$_2$ | 41 | Triphenylborane | 57 |
| Ni(CN)$_2$ | 8 | Ni(CN)$_2$ | 13 |
| Adiponitrile | 25 | Adiponitrile | 22 |
| Methylglutaronitrile | 15 | Methylglutaronitrile | 2 |
| Pentenenitriles | 4 | Pentenenitriles | 3 |
| Cyclohexane | 3 | Cyclohexane | 3 |
| | | Balance - Miscellaneous Organics | |

The liquid discharge from centrifuge 17 is distilled in column 19 to recover residual 3-pentenenitrile, cyclohexane and other volatiles overhead (line 20).

Stream 18 was normally sent to waste.

Attempts to further remove desirable compounds such as adiponitrile from stream 18 by thermal treatment, e.g., by heating under vacuum, result in excessive degradation of the organics resulting in a residue of tar-like consistency if sufficient heat is supplied to achieve a practical rate of removal. Although desirable compounds in this stream can be extracted with known solvents such as methanol, such solvents are foreign to the hydrocyanation system and require extensive refining to separate the solvent from the nitriles before the nitriles can be recycled or recovered. It has been discovered that the desired by-products and products from the hydrocyanation reaction, principally adiponitrile, can be recovered from this stream and returned to the process by employing one of the intermediates of the process as a solvent and extracting the above-described stream with that solvent. Accordingly, stream 18 is passed to extractor 25 where it is thoroughly contacted with mono-olefinically unsaturated nitrile introduced via line 26. The solvent/extractant is advantageously 3-pentenenitrile and in practical application is found as a recycle stream in the hydrocyanation process and particularly a stream from the treatment of stream 5.

Two typical streams which can be employed as extractants (line 26) contain the following compounds in the amounts indicated in Table II. Abbreviations following the named compounds are used in the following portion of the specification.

TABLE II

| Compound | Concentration (% by weight) | |
|---|---|---|
| | Stream 1 | Stream 2 |
| Cis-2-pentenenitrile (C2PN) | 0 | 2.0 |
| Cis-2-methyl-2-butene-nitrile (C2M2BN) | 2.0 | 9.0 |
| Valeronitrile (VN) | 0 | 3.0 |
| Trans-2-pentenenitrile (T2PN) | 0.5 | 5.0 |
| Trans-3-pentenenitrile (T3PN) | 88.0 | 55.0 |
| 4-pentenenitrile (4PN) | 2.0 | 3.0 |
| Cis-3-pentenenitrile (C3PN) | 3.0 | 10.0 |
| Ethyl succinonitrile (ESN) | .2 | 1.5 |
| 2-methylglutaronitrile (MGN) | 0.5 | 3.0 |
| adiponitrile (ADN) | 0.2 | 5.0 |
| Balance - Miscellaneous Organics | | |

After thorough contact of the extractant (line 26) with the sludge (line 18), the resultant mixture is directed to a suitable separator 27 via line 28. The liquid from separator 27 (line 29) can be returned to the hydrocyanation process, e.g., directly to product recovery portion or to the hydrocyanation step or indirectly to other portions of the process after additional refining and/or separation depending upon the demand for the various components of the extract. The treated solids can now be directed to drier 30 via line 31 since the tar-forming organics have been extracted and replaced with more volatile nitriles which are readily removed without excessive degradation. Volatile materials which are driven from the solids during drying (line 32) can be condensed and combined with the solution in line 29. A typical analysis of the solution (line 29) and the volatile material from dryer 30 (line 32) is set forth below in Table III.

TABLE III

| Compound | Concentration (% by weight) | |
|---|---|---|
| | Stream 29 | Stream 32 |
| C-2-PN | 0.2 | 0 |
| C2M2BN | 2.5 | 1.2 |
| VN | 0.2 | 0 |
| T2PN | 0.2 | 0.4 |
| T3PN | 80.0 | 82.0 |
| 4PN | 1.5 | 1.5 |
| C3PN | 2.6 | 3.3 |
| ESN | 0.2 | 0.2 |
| MGN | 2.2 | 2.1 |
| ADN | 10.0 | 1.8 |

The solids (line 33) from dryer 30 can be disposed of in a conventional manner or treated to recover catalyst components.

Nitriles which are compatible with the hydrocyanation reaction are operable as extractants in the present process. Such nitriles include those having a boiling point at atmospheric pressure of below about 250° C and having from 5-10 carbon atoms which are sufficiently volatile so that they can be rapidly removed from the solid catalyst residue at the temperatures below about 215° C and preferably below 200° C in order to minimize thermal decomposition of the residue. It is preferred to employ nitriles which are already present in the reaction system for example, 3-pentenenitrile and mixtures of pentenenitriles which are found in available process streams as discussed hereinabove. Especially preferred extractants consist essentially of pentenenitriles and, more particularly, consist essentially of 3-pentenenitrile, 2-pentenenitrile and mixtures of the foregoing. Substantial amounts of other compounds including MGN and ADN may also be present without adversely affecting the extraction efficiency of the olefinic nitrile.

Extractants such as acetone and methanol should be avoided because they can solubilize metals which metals can cause problems when returned to the process.

The extraction of catalyst slurry or residue with the olefinically unsaturated nitrile can be conducted under a variety of conditions, i.e., at temperatures in the range of ambient to 80° C and at a weight ratio of olefinic nitriles to slurry of from 0.5:1 to 15:1 and preferably 3:1 to 6:1. Sufficient mixing should be provided for contact of the solvent with the slurry according to known procedures for effective extraction.

The following examples are presented to illustrate but not to restrict the present invention. Parts and percentages are by weight unless otherwise specified.

EXAMPLE 1

Approximately 100 grams of a catalyst slurry and 400 grams of a mixture of pentenenitriles were introduced into a 1 liter flask containing a magnetic stirrer. The compositions of the catalyst slurry and the nitrile mixture are set forth hereinbelow.

| Slurry | |
|---|---|
| Compound | Concentration % by weight |
| $Zn(NH_3)_2Cl_2$ | 39 |
| $Ni(CN)_2$ | 5.3 |
| MGN | 25.2 |
| ADN | 17.6 |
| ESN | 3.3 |
| Balance Miscellaneous nitriles and organics. | |

| Nitrile Mixture (Solvent) | |
|---|---|
| Compound | Concentration % by weight |
| MGN | 1.1 |
| ADN | 4.1 |
| 3PN | 70.0 |
| ESN | .04 |
| 2PN + butadiene | 10.0 |
| Balance Miscellaneous nitriles and organics. | |

The mixture was agitated at 25° C for 15 minutes following which the liquid and solids were separated by vacuum filtration. The resulting filter cake was then washed with an additional 100 grams of the pentenenitrile mixture at room temperature and then dried for 1 hour at 80° C under a vacuum of 4 inches of mercury absolute. A bleed of nitrogen was maintained over the solids to assist drying. The vapors that evolved during drying were condensed and collected.

The condensate from drying, the wash and the filtrate were combined (541.5 grams) and analyzed to contain (% by weight) ADN 6.9, MGN 5.4, ESN 0.7 with a substantial portion of remainder being 2 and 3 pentenenitriles along with minor amounts of other organics. Approximately 96% of the ADN and 95% of the MGN originally present in the slurry were recovered in the combined streams.

It was determined that the nitrile-slurry mixture could be agitated for periods of 5-30 minutes without adversely affecting the foregoing results.

EXAMPLE 2

Approximately one part by weight of catalyst slurry having the composition set forth below was combined with six parts by weight of refined 3-pentenenitrile (approximately 96% pure).

| Catalyst Slurry | |
|---|---|
| Compound | Concentration % by weight |
| $Zn(NH_3)_2Cl_2$ | 40.0 |
| $Ni(CN)_2$ | 6.3 |
| MGN | 8.4 |
| ADN | 24.0 |
| 3PN | 1.4 |
| Balance Misc. nitriles and organics | |

The resultant mixture was agitated at 25° C for 15 minutes following which the liquid and solids were separated by centrifugation. The solids were dried as in Example 1. The dry solids contained 8.3% Ni and 30.7% Zn. The liquid from the centrifuge and the condensate from the drying were combined and analyzed. The results of the analysis follows:

| Combined Extract | |
|---|---|
| Compound | Concentration % by weight |
| ADN | 3.7 |
| MGN | 2.8 |
| 3PN | 83.7 |
| Balance misc. nitriles | |

About 92.5% of the adiponitrile originally present in the catalyst slurry was recovered.

EXAMPLE 3

The procedure of Example 1 was repeated except that the ratio of the pentenenitrile mixture to catalyst slurry was varied from 3/1 to 6/1 with the result that approximately 90-94% of the desired products, e.g., adiponitrile were recovered at the lower ratio while approximately 93-97% of the desired products were recovered at the higher ratios.

EXAMPLE 4

Approximately 10 grams of catalyst residue obtained from the hydrocyanation of butadiene as described hereinabove using triphenylborane as the promoter having the following elemental analysis was thoroughly mixed with 50 ml of refined 3PN on the frit of a vacuum filter at room temperature.

| Carbon | Hydrogen | Nitrogen | Nickel | Phosphorus | Boron |
|---|---|---|---|---|---|
| | | (% by weight) | | | |
| 72.20 | 6.22 | 11.25 | 5.15 | 1.13 | 1.96 |

After thorough contact with the 3PN the solids were filtered and dried under vacuum for 12 hours at room temperature to yield 6.88 grams of extracted residue. The filtrate was found to contain 2.38 weight % ADN and 0.13% MGN. Essentially no ADN was detected when the 3PN was replaced with cyclohexane and the above procedure was repeated.

What is claimed is:

1. An process for the recovery of organic nitriles from a waste stream containing products, by-products and catalyst residue obtained from a process for the production of adiponitrile by the hydrocyanation of butadiene in the presence of a zero-valent nickel catalyst wherein said waste stream is obtained after recovery of product from the hydrocyanation reaction which process comprises extracting said waste stream with an extractant consisting essentially of organic nitriles having about 5-10 carbon atoms and having a boiling point below about 250° C at atmospheric pressure, separating the resultant extract from the insoluble material at a temperature below about 215° C and thereafter returning at least a portion of the extract to the hydrocyanation process.

2. The process of claim 1 wherein the extractant consists essentially of olefinically unsaturated nitriles selected from the class consisting of 3-pentenenitrile, 2-pentenenitrile and mixtures thereof.

3. The process of claim 1 wherein the weight ratio of extractant to waste stream is maintained at at least 0.5/1.

4. The process of claim 3 wherein said ratio is maintained in the range 3/1-6/1.

* * * * *